(12) United States Patent
Soffin et al.

(10) Patent No.: US 7,820,609 B2
(45) Date of Patent: *Oct. 26, 2010

(54) MILD, STRUCTURED, MULTI-PHASE PERSONAL CLEANSING COMPOSITIONS COMPRISING DENSITY MODIFIERS

(75) Inventors: Daniel Jacob Soffin, Colerain Township, OH (US); Scott William Syfert, Ft. Mitchell, KY (US); Karl Shiqing Wei, Mason, OH (US); Edward Dewey Smith, III, Mason, OH (US); Mark Richard Sine, New Richmond, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/451,245

(22) Filed: Jun. 12, 2006

(65) Prior Publication Data

US 2007/0072781 A1 Mar. 29, 2007

Related U.S. Application Data

(63) Continuation-in-part of application No. 11/400,634, filed on Apr. 7, 2006.

(60) Provisional application No. 60/670,785, filed on Apr. 13, 2005, provisional application No. 60/680,114, filed on May 12, 2005, provisional application No. 60/680,149, filed on May 12, 2005.

(51) Int. Cl.
*A61K 7/00* (2006.01)

(52) U.S. Cl. .......................... 510/130; 510/156; 510/424; 510/425; 510/426; 510/428

(58) Field of Classification Search .................. None
See application file for complete search history.

(56) References Cited

U.S. PATENT DOCUMENTS

| | | | |
|---|---|---|---|
| 2,438,091 A | 3/1948 | Lynch | |
| 2,528,378 A | 10/1950 | Mannheimer | |
| 2,658,072 A | 11/1953 | Kosmin | |
| 2,798,053 A | 7/1957 | Brown | |
| 3,479,429 A | 11/1969 | Morshauser et al. | |
| 3,533,955 A | 10/1970 | Pader et al. | |
| 3,615,972 A | 10/1971 | Morehouse, Jr. et al. | |
| 3,929,678 A | 12/1975 | Laughlin et al. | |
| 3,937,811 A | 2/1976 | Papantoniou et al. | |
| 3,951,679 A | 4/1976 | Bernhard et al. | |
| 4,159,028 A | 6/1979 | Barker et al. | |
| 4,263,363 A | 4/1981 | Buck et al. | |
| 4,335,103 A | 6/1982 | Barker et al. | |
| 4,379,753 A | 4/1983 | Bolich, Jr. | |
| 4,387,090 A | 6/1983 | Bolich, Jr. | |
| 4,425,322 A | 1/1984 | Harvey et al. | |
| 4,509,949 A | 4/1985 | Huang et al. | |
| 4,518,578 A | 5/1985 | Hayes et al. | |
| 4,705,681 A | 11/1987 | Maes et al. | |
| 4,899,877 A | 2/1990 | Kiernan | |
| 4,966,205 A | 10/1990 | Tanaka | |
| 4,980,155 A | 12/1990 | Shah et al. | |
| 5,011,690 A | 4/1991 | Garvey et al. | |
| 5,052,557 A | 10/1991 | Contino et al. | |
| 5,059,414 A | 10/1991 | Dallal et al. | |
| 5,087,445 A | 2/1992 | Haffey et al. | |
| 5,228,189 A | 7/1993 | Driller et al. | |
| 5,248,495 A | 9/1993 | Patterson et al. | |
| RE34,584 E | 4/1994 | Grote et al. | |
| 5,393,450 A | 2/1995 | Shana'a et al. | |
| 5,451,396 A | 9/1995 | Villars | |
| 5,455,035 A | 10/1995 | Guerrero et al. | |
| 5,487,168 A | 1/1996 | Geiner et al. | |
| 5,487,884 A | 1/1996 | Bissett et al. | |
| 5,530,054 A | 6/1996 | Tse et al. | |
| 5,556,628 A | 9/1996 | Derian et al. | |
| 5,612,307 A | 3/1997 | Chambers et al. | |
| 5,635,171 A | 6/1997 | Nadaud et al. | |
| 5,652,228 A | 7/1997 | Bissett | |
| 5,661,189 A | 8/1997 | Grievson et al. | |
| 5,681,852 A | 10/1997 | Bissett | |
| 5,716,920 A | 2/1998 | Glenn, Jr. et al. | |
| 5,851,978 A | 12/1998 | Shana'a | |
| 5,885,948 A | 3/1999 | Glenn, Jr. et al. | |
| 5,929,019 A | 7/1999 | Puvvada et al. | |
| 5,932,203 A | 8/1999 | Coffindaffer et al. | |
| 5,935,561 A | 8/1999 | Inman et al. | |
| 5,947,335 A | 9/1999 | Milio et al. | |
| 5,952,286 A | 9/1999 | Puvvada et al. | |
| 5,965,500 A | 10/1999 | Puvvada | |
| 6,051,541 A | 4/2000 | Neuser et al. | |
| 6,080,707 A | 6/2000 | Glenn, Jr. et al. | |
| 6,114,290 A | 9/2000 | Lyle et al. | |

(Continued)

FOREIGN PATENT DOCUMENTS

CA 2246316 6/1998

(Continued)

OTHER PUBLICATIONS

C.D. Vaughan, "Solubility, Effects in Product, Package, Penetration and Preservation," Cosmetics and Toiletries, vol. 103, Oct. 1988.

(Continued)

*Primary Examiner*—Necholus Ogden, Jr.
(74) *Attorney, Agent, or Firm*—Hilary A. Reinhardt; Mark A. Charles

(57) ABSTRACT

A mild, multi-phase cleansing composition is described that includes a cleansing phase including a structured surfactant component has a first density; a benefit phase includes an emulsion, the benefit phase has a second density and a density modifier; wherein the first density differs from the second density by less than 0.15 g/cm$^3$; the structured surfactant component includes at least one surfactant and provides a Total Lather Volume of at least about 600 ml. The emulsion is either an oil in water or an oil in water emulsion.

20 Claims, No Drawings

U.S. PATENT DOCUMENTS

| | | |
|---|---|---|
| 6,174,845 B1 | 1/2001 | Rattinger et al. |
| 6,176,391 B1 | 1/2001 | Rehkemper et al. |
| 6,176,395 B1 | 1/2001 | Abbott et al. |
| 6,190,648 B1 | 2/2001 | Kouzu et al. |
| 6,194,364 B1 | 2/2001 | Glenn, Jr. |
| 6,213,166 B1 | 4/2001 | Thibiant et al. |
| 6,245,323 B1 | 6/2001 | Christie et al. |
| 6,245,344 B1 | 6/2001 | Thibiant et al. |
| 6,255,264 B1 | 7/2001 | Fleurot et al. |
| 6,267,978 B1 * | 7/2001 | Sang et al. .................. 424/401 |
| 6,268,322 B1 | 7/2001 | St. Lewis et al. |
| 6,294,179 B1 | 9/2001 | Lee et al. |
| 6,306,806 B1 | 10/2001 | St. Lewis et al. |
| 6,335,312 B1 | 1/2002 | Coffindaffer et al. |
| 6,340,723 B1 | 1/2002 | Nitta et al. |
| 6,362,156 B1 | 3/2002 | Hsu et al. |
| 6,367,519 B2 | 4/2002 | Thibiant et al. |
| 6,383,999 B1 | 5/2002 | Coyle et al. |
| 6,395,691 B1 | 5/2002 | Tsaur |
| 6,429,177 B1 | 8/2002 | Salmon et al. |
| 6,491,932 B1 | 12/2002 | Ramin et al. |
| 6,495,498 B2 | 12/2002 | Niemiec et al. |
| 6,506,391 B1 | 1/2003 | Biatry |
| 6,516,838 B2 | 2/2003 | Thibiant et al. |
| 6,517,939 B1 | 2/2003 | Ramin et al. |
| 6,533,873 B1 | 3/2003 | Margosiak et al. |
| 6,534,456 B2 | 3/2003 | Hayward et al. |
| 6,534,457 B2 | 3/2003 | Mitra |
| 6,645,511 B2 | 11/2003 | Aronson et al. |
| 6,673,371 B2 | 1/2004 | Brown et al. |
| 6,673,755 B2 | 1/2004 | Wei et al. |
| 6,682,726 B2 | 1/2004 | Marchesi et al. |
| 6,699,488 B2 | 3/2004 | Deckner et al. |
| 6,759,376 B2 | 7/2004 | Zhang et al. |
| 6,764,991 B2 | 7/2004 | Puvvada et al. |
| 6,773,811 B2 | 8/2004 | Ferguson et al. |
| 6,780,826 B2 | 8/2004 | Zhang et al. |
| 6,787,511 B2 | 9/2004 | Patel et al. |
| 6,797,683 B2 | 9/2004 | Shana'a et al. |
| 6,903,057 B1 | 6/2005 | Tsaur |
| 6,924,256 B2 | 8/2005 | Massaro et al. |
| 2001/0036467 A1 | 11/2001 | Thibiant et al. |
| 2002/0004468 A1 | 1/2002 | Hodge et al. |
| 2002/0010110 A1 | 1/2002 | Hayward et al. |
| 2003/0049282 A1 | 3/2003 | Aaronson et al. |
| 2003/0054019 A1 | 3/2003 | Aronson et al. |
| 2003/0068287 A1 | 4/2003 | Ansara et al. |
| 2003/0152540 A1 | 8/2003 | Putman et al. |
| 2003/0161852 A1 | 8/2003 | Miller et al. |
| 2003/0180246 A1 | 9/2003 | Frantz et al. |
| 2003/0222100 A1 | 12/2003 | Husband et al. |
| 2004/0033914 A1 | 2/2004 | Patel et al. |
| 2004/0048757 A1 | 3/2004 | Zhang et al. |
| 2004/0048758 A1 | 3/2004 | Zhang et al. |
| 2004/0057920 A1 | 3/2004 | Focht et al. |
| 2004/0058920 A1 | 3/2004 | Jover et al. |
| 2004/0092415 A1 * | 5/2004 | Focht et al. .................. 510/130 |
| 2004/0105827 A1 | 6/2004 | Grimm et al. |
| 2004/0158940 A1 | 8/2004 | Wells et al. |
| 2004/0219119 A1 | 11/2004 | Wei et al. |
| 2004/0223929 A1 | 11/2004 | Clapp et al. |
| 2004/0223991 A1 | 11/2004 | Wei et al. |
| 2004/0235693 A1 | 11/2004 | Wei et al. |
| 2004/0242706 A1 | 12/2004 | Wiersema et al. |
| 2004/0248748 A1 * | 12/2004 | Wei et al. .................. 510/130 |
| 2005/0020468 A1 | 1/2005 | Frantz et al. |
| 2005/0100570 A1 | 5/2005 | Wei et al. |
| 2005/0143269 A1 | 6/2005 | Wei et al. |
| 2005/0191449 A1 | 9/2005 | Funato et al. |
| 2005/0192187 A1 | 9/2005 | Wagner et al. |
| 2005/0192188 A1 | 9/2005 | Wagner et al. |
| 2005/0192189 A1 * | 9/2005 | Wagner et al. .................. 510/130 |
| 2005/0238680 A1 | 10/2005 | Stella et al. |
| 2005/0276768 A1 | 12/2005 | Wei et al. |
| 2006/0002880 A1 | 1/2006 | Peffly et al. |
| 2006/0102654 A1 | 5/2006 | Seys et al. |
| 2006/0118139 A1 | 6/2006 | Fausnight et al. |
| 2006/0182699 A1 | 8/2006 | Taylor et al. |
| 2006/0191589 A1 | 8/2006 | McCall et al. |
| 2006/0252662 A1 | 11/2006 | Soffin et al. |
| 2006/0276357 A1 | 12/2006 | Smith et al. |
| 2007/0155637 A1 | 7/2007 | Smith, III et al. |
| 2007/0163990 A1 | 7/2007 | Escobosa et al. |
| 2007/0167338 A1 | 7/2007 | McHugh et al. |
| 2007/0187274 A1 | 8/2007 | Dalea et al. |
| 2007/0248562 A1 | 10/2007 | Berry et al. |
| 2007/0280976 A1 | 12/2007 | Taylor et al. |

FOREIGN PATENT DOCUMENTS

| | | |
|---|---|---|
| CH | 678488 A5 | 9/1991 |
| DE | 196 50 952 A | 6/1998 |
| DE | 198 54 086 A | 5/2000 |
| EP | 0056219 A1 | 7/1982 |
| EP | 0 078138 A2 | 5/1983 |
| EP | 0112807 A2 | 7/1984 |
| EP | 0320473 A1 | 6/1989 |
| EP | 0348372 A2 | 12/1989 |
| EP | 0 331617 B | 4/1992 |
| EP | 0486080 A2 | 5/1992 |
| EP | 1 108421 A2 | 6/2001 |
| EP | 1 005849 B1 | 9/2001 |
| EP | 1174360 A1 | 1/2002 |
| EP | 1 064918 B1 | 9/2002 |
| EP | 0 907345 B1 | 5/2003 |
| EP | 1529517 A2 | 5/2005 |
| GB | 1277324 A | 6/1972 |
| GB | 2310398 A | 8/1997 |
| JP | 02184884 | 7/1990 |
| JP | 05254528 | 10/1993 |
| JP | 2000229817 A | 8/2000 |
| JP | 2002-128639 A | 5/2002 |
| JP | 2002-138010 A | 5/2002 |
| WO | WO 90/13283 A1 | 11/1990 |
| WO | WO-92/12212 A1 | 7/1992 |
| WO | WO 94/10973 A1 | 5/1994 |
| WO | WO 97/17938 A1 | 5/1997 |
| WO | WO 98/27193 A1 | 6/1998 |
| WO | WO 99/09952 * | 3/1999 |
| WO | WO 99/38489 A1 | 8/1999 |
| WO | WO 99/38491 A1 | 8/1999 |
| WO | WO 00/75240 A1 | 12/2000 |
| WO | WO 01/01931 A1 | 1/2001 |
| WO | WO-01/64180 A1 | 9/2001 |
| WO | WO 01/70193 A2 | 9/2001 |
| WO | WO 01/70926 A1 | 9/2001 |
| WO | WO 02/100358 A1 | 12/2002 |
| WO | WO 03/055456 A1 | 7/2003 |
| WO | WO 03/105796 A1 | 12/2003 |
| WO | WO 2004/018609 A1 | 3/2004 |
| WO | WO 2004/026276 A1 | 4/2004 |
| WO | WO 2004/050055 * | 6/2004 |
| WO | WO 2004/050055 A1 | 6/2004 |
| WO | WO-2004/083351 A1 | 9/2004 |
| WO | WO 2004/096162 * | 11/2004 |
| WO | WO-2004/098559 A2 | 11/2004 |
| WO | WO-2004/100919 A1 | 11/2004 |
| WO | WO-2005/048959 A1 | 6/2005 |
| WO | WO-2005/065638 A1 | 7/2005 |
| WO | WO 2005/067875 A1 | 7/2005 |
| WO | WO 2005/084614 * | 9/2005 |

| | | | |
|---|---|---|---|
| WO | WO-2005/084616 A1 | 9/2005 | |
| WO | WO-2005/123031 A1 | 12/2005 | |

OTHER PUBLICATIONS

Crank, Mathematics of Duffusion, 2nd Edition, p. 63.
CTFA International Cosmetic Ingredient Dictionary, Fourth Edition, 1991, pp. 12 and 80.
Milton, Introduction to Probability and Statistics, 4th Edition, p. 317 (Section 9.2: Testing Hypotheses on a Proportion).
KOBO brochure, "Treated Pigments" (May 2000).
Office Action from U.S. Appl. No. 10/841,174, mailed Jan. 12, 2010 (27 pages).
Office Action from U.S. Appl. No. 10/963,166, mailed Feb. 16, 2010 (14 pages).
Office Action from U.S. Appl. No. 11/894,143, mailed Nov. 9, 2009 (8 pages).

* cited by examiner

MILD, STRUCTURED, MULTI-PHASE PERSONAL CLEANSING COMPOSITIONS COMPRISING DENSITY MODIFIERS

CROSS REFERENCE TO RELATED APPLICATIONS

This application is a continuation in part of U.S. application Ser. No. 11/400,634, filed Apr. 7, 2006, pending, which claims the benefit of U.S. Provisional application Ser. No. 60/670,785 filed on Apr. 13, 2005 and U.S. Provisional application Ser. No. 60/680,114 filed on May 12, 2005 and U.S. Provisional application Ser. No. 60/680,149 filed on May 12, 2005.

FIELD OF THE INVENTION

The present invention relates to a mild, structured, multi-phase, personal cleansing composition that comprises a density modifier wherein the first density of the structured surfactant component differs from the second density of the benefit component by less than 0.15 g/cm$^3$.

BACKGROUND OF THE INVENTION

Personal cleansing compositions that attempt to provide skin-conditioning benefits are known. Many of these compositions are aqueous systems comprising an emulsified conditioning oil or other similar materials in combination with a lathering surfactant. Although these products provide both conditioning and cleansing benefits, it is often difficult to formulate a product that deposits sufficient amount of skin conditioning agents on skin during use. In order to combat emulsification of the skin conditioning agents by the cleansing surfactant, large amounts of the skin conditioning agent are added to the compositions. However, this introduces another problem associated with these dual cleansing and conditioning products. Raising the level of skin conditioning agent in order to achieve increased deposition negatively affects product stability.

It is known that dispersions and emulsions in personal cleansing compositions that comprise structured surfactants exhibit buoyant forces due to the difference in density between the continuous structured surfactant component, and the benefit component. For example, when the benefit component comprises a hydrophobic material such as a triglyceride or a hydrocarbon material, the density of the dispersed phase is about 0.9 gm/cm$^3$, whereas the density of the continuous structured surfactant component is about 1.0 gm/cm$^3$. When the buoyant force of a benefit component exceeds the local value of the yield stress of the continuous structured surfactant component, the droplet can rise through the continuous phase in a process called creaming. Given a sufficient amount of creaming, exacerbated by coalescence of the benefit component, phase separation can occur as the product becomes unstable, e.g., during shipping and extended storage on a store shelf.

Accordingly, the need still remains for a multi-phase, blended personal cleansing composition that provides both cleansing and improved skin conditioning benefits which remains for a personal cleansing composition comprising two phases in physical contact that remain stable for long periods of time.

SUMMARY OF THE INVENTION

The present invention relates to a mild, multi-phase cleansing composition that comprises a cleansing phase comprising a structured surfactant component, the cleansing phase has a first density. The benefits phase comprises and emulsion and has a second density and a density modifier; wherein the first density differs from the second density by less than 0.15 g/cm$^3$; the structured surfactant component comprises at least one surfactant and provides a Total Lather Volume of at least about 600 ml. The benefit phase may comprise a water in oil emulsion or an oil in water emulsion.

The inventors believe that when the structured surfactant component comprises low density particles such that all parts of the composition are exposed to buoyant forces by the dispersed low density phase and the low density particles, creaming and phase separation are mitigated and the composition can be stabilized even under harsh conditions such as high temperature shipping and storage conditions.

The inventors believe that mild, multi-phase personal cleansing compositions can be formulated with enhanced stability by density matching of the cleansing phase and the benefit phase by incorporating density modifiers in the cleansing phase and/or the benefit phase. The inventor believe that a multi-phase personal cleansing composition containing both cleansing and benefit phases with high levels of benefit agents without compromising product lather performance and stability can be formulated and blended to provide improved cosmetics and skin feel during and after application while also providing excellent skin conditioning and cleansing benefits.

DETAILED DESCRIPTION OF THE INVENTION

The term "ambient conditions" as used herein, refers to surrounding conditions at one (1) atmosphere of pressure, 50% relative humidity, and 25° C.

By the term "multi-phase" or "multi-phase" as used herein, is meant that the phases of the present compositions occupy separate but distinct physical spaces inside the package in which they are stored, but are in direct physical contact with one another (i.e., they are not separated by a barrier and they are not emulsified or mixed to any significant degree). In one preferred embodiment of the present invention, the "multi-phase" personal cleansing compositions comprise at least two visually distinct phases which are present within the container as a visually distinct pattern. The pattern results from the combination of the "multi-phase" composition by a process herein described. The "patterns" or "patterned" include but are not limited to the following examples: striped, marbled, rectilinear, interrupted striped, check, mottled, veined, clustered, speckled, geometric, spotted, ribbons, helical, swirl, arrayed, variegated, textured, grooved, ridged, waved, sinusoidal, spiral, twisted, curved, cycle, streaks, striated, contoured, anisotropic, laced, weave or woven, basket weave, spotted, and tessellated. Preferably the pattern is selected from the group consisting of striped, geometric, marbled, and combinations thereof.

In a preferred embodiment, the pattern may be relatively uniform across the dimension of the package; however, the pattern may be uneven, wavy, or non-uniform in dimension and does not extend across the entire dimension of the package. If striped, the size of the stripes can be at least about 0.1 mm in width and 10 mm in length, preferably at least about 1 mm in width and at least 20 mm in length as measured from the package exterior. The phases may be various different colors, and/or include particles, glitter or pearlescent agents in at one of the phases in order to offset its appearance from the other. A phase generally occupies a space or spaces having dimensions larger than the colloidal or sub-colloidal components it comprises. A phase may also be constituted or reconstituted, collected, or separated into a bulk phase in order to observe its properties.

The term "multi-phase personal cleansing composition" as used herein, refers to compositions intended for topical application to the skin or hair. Preferably, the compositions of the present invention are rinse-off formulations, in which the product is applied topically to the skin or hair and then is subsequently rinsed within minutes from the skin or hair with water, or otherwise wiped off using a substrate with deposition of a portion of the composition. The compositions also may be used as shaving aids.

The term "surfactant component" as used herein means the total of all anionic, nonionic, amphoteric, zwitterionic and cationic surfactants in a phase. When calculations are based on the surfactant component, water and electrolyte are excluded from the calculations.

The term "structured," as used herein means having a rheology that confers stability on the multi-phase composition. The degree of structure is determined by characteristics determined by one or more of the following methods the Yield Stress Method, or the Zero Shear Viscosity Method or by the Ultracentrifugation Method, all in the Test Methods below. Accordingly, a surfactant phase of the multi-phase composition of the present invention is considered "structured," if the surfactant phase has one or more of the following properties described below according to the Yield Stress Method, or the Zero Shear Viscosity Method or by the Ultracentrifugation Method. A surfactant phase is considered to be structured, if the phase has one or more of the following characteristics:

A. a Yield Stress of greater than about 0.1 Pascal (Pa), more preferably greater than about 0.5 Pa, even more preferably greater than about 1.0 Pa, still more preferably greater than about 2.0 Pa, still even more preferably greater than about 3 Pa, and even still even more preferably greater than about 5 Pa as measured by the Yield Stress and Zero Shear Viscosity Method described hereafter:

B. a Zero Shear Viscosity of at least about 500 Pascal-seconds (Pa-s), preferably at least about 1,000 Pa-s, more preferably at least about 1,500 Pa-s, even more preferably at least about 2,000 Pa-s; or C. a Structured Domain Volume Ratio as measured by the Ultracentrifugation Method described hereafter, of greater than about 40%, preferably at least about 45%, more preferably at least about 50%, more preferably at least about 55%, more preferably at least about 60%, more preferably at least about 65%, more preferably at least about 70%, more preferably at least about 75%, more preferably at least about 80%, even more preferably at least about 85%.

As used herein "substantially free" means that the composition or phase comprises less than about 5%, preferably less than 3%, preferably less than about 1%, more preferably less than about 0.5%, more preferably less than about 0.25%, and most preferably less than about 0.1%, by weight of the composition or phase of a stated ingredient.

The multi-phase personal cleansing composition of the present invention is typically extrudable or dispensible from a package. The multi-phase personal cleansing compositions typically exhibit a viscosity of from about 1,500 centipoise (cP) to about 1,000,000 cP, as measured by the Viscosity Method as described in copending application Ser. No. 10/841,174 filed on May 7, 2004 titled "Multi-phase Personal Care Compositions."

When evaluating a structured multi-phase personal cleansing composition, by the methods described herein, preferably each individual phase is evaluated prior to combining, unless otherwise indicated in the individual methodology. However, if the phases are combined, each phase can be separated by centrifugation, ultracentrifugation, pipetting, filtering, washing, dilution, concentration, or combination thereof, and then the separate components or phases can be evaluated. Preferably, the separation means is chosen so that the resulting separated components being evaluated is not destroyed and the composition and distribution of components therein is not substantially altered by the separation means, so that it is representative of the component as it exists in the structured multi-phase personal cleansing composition.

The multi-phase personal cleansing compositions of the present invention comprise at least two phases, but the compositions, a third phase, a fourth phase and so on. The ratio of a first phase to a second phase is preferably from about 1:99 to about 99:1, preferably from about 90:10 to about 10:90, more preferably from about 80:20 to about 20:80, even more preferably from about 70:30 to about 30:70, still even more preferably from about 60:40 to about 40:60, even still even more preferably about 50:50.

The multi-phase personal cleansing composition of the present invention can comprise a cleansing phase. The multi-phase personal cleansing composition typically comprises from about 1% to about 99%, and more preferably from about 20% to about 50%, by weight of the composition, of the cleansing phase.

The cleansing phase typically provides a Total Lather Volume of at least about 600 ml, preferably greater than about 800 ml, more preferably greater than about 1000 ml, even more preferably greater than about 1200 ml, and still more preferably greater than about 1500 ml, as measured by the Lather Volume Test described hereafter. The cleansing phase preferably has a Flash Lather Volume of at least about 300 ml, preferably greater than about 400 ml, even more preferably greater than about 500 ml, as measured by the Lather Volume Test described hereafter.

The multi-phase personal cleansing composition preferably comprises a structured surfactant component at concentrations ranging from about 2% to about 23.5%, more preferably from about 3% to about 21%, even more preferably from about 4% to about 20.4%, still more preferably from about 5% to about 20%, still even more preferably from about 13% to about 18.5%, and even still even more preferably from about 14% to about 18%, by weight of the cleansing phase.

The cleansing phase comprising the structured surfactant component is preferably a structured domain comprising surfactants. The structured domain enables the incorporation of high levels of benefit components in a separate phase that are not emulsified in the composition. In a preferred embodiment, the structured domain is an opaque structured domain which is preferably a lamellar phase that preferably produces a lamellar gel network. The lamellar phase can provide resistance to shear, adequate yield to suspend particles and droplets and at the same time provides long term stability, since it is thermodynamically stable. The lamellar phase tends to have a higher viscosity thus minimizing the need for viscosity modifiers.

The structured surfactant component preferably comprises a lathering surfactant or a mixture of lathering surfactants. The structured surfactant component comprises surfactants suitable for application to the skin or hair which are otherwise compatible with the other essential ingredients in the multi-phase personal cleansing composition including water. Suitable surfactants are described in McCutcheon's, Detergents and Emulsifiers, North American edition (1986), published by allured Publishing Corporation; and McCutcheon's, Functional Materials, North American Edition (1992); and in U.S. Pat. No. 3,929,678 issued to Laughlin, et al on Dec. 30, 1975. These surfactants include anionic, nonionic, cationic, zwitterionic, amphoteric surfactants, soap, or combinations thereof.

Preferably, anionic surfactant comprises at least 40% of the structured surfactant component, more preferably from about 45% to about 95% of the structured surfactant component, even more preferably from about 50% to about 90%, still more preferably from about 55% to about 85%, and even still most preferably at least about 60% of the structured surfactant component comprises anionic surfactant which may be linear or branched. The cleansing phase or structured surfactant component preferably comprises at least one branched anionic surfactant. A surfactant molecule is branched when the hydrocarbon tail of the surfactant molecule comprises at least one ternary or quaternary carbon atom, such that a methyl, ethyl, propyl, butyl, pentyl or hexyl side chain extends from the hydrocarbon backbone. The hydrocarbon backbone is described by the longest hydrocarbon length in the hydrocarbon tail. A side chain in the branched hydrocarbon of a surfactant molecule can be described by its position on the backbone, counting from the first carbon attached to a hydrophilic atom, enumerated as carbon number 1, the adjacent carbon on the backbone being carbon number 2, and so on. Side chains are also described by their length, a single carbon side chain denoted methyl; a 2-carbon length denoted ethyl, and so on. Side chains that have their own branching are denoted by conventional nomenclature techniques, e.g., isopropyl, but are less common. Anionic surfactant molecules which do not have branching are linear anionic surfactant molecules, and surfactants comprising a preponderance of linear anioinic surfactant molecules as indicated hereafter are linear anionic surfactants. Preferred linear anionic surfactants for use in the structured surfactant phase of the multi-phase, personal cleansing composition include ammonium lauryl sulfate, ammonium laureth sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, potassium lauryl sulfate, and combinations thereof.

Because an anionic surfactant typically comprises a mixture of different types of surfactant molecules, anionic surfactants can be called linear or branched depending on the relative amounts of individual surfactant molecules of different types that comprise the anionic surfactant. For example, sodium tridecyl sulfate and sodium trideceth sulfate can be called branched surfactants because they typically comprise nearly all (>95%) branched surfactant molecules. For the purposes of the present invention, an anionic surfactant is considered branched surfactant when at least 10% of its hydrocarbon chains are branched molecules. Branching information for many surfactants is typically known or obtainable from suppliers of branched alcohol feedstocks and described in commonly owned U.S. Patent Application Ser. No. 60/680,149 entitled "Structured Multi-phased Personal Cleansing Compositions Comprising Branched Anioinic Surfactants", filed on May 12, 2005, by Smith, et al.

Branched anionic surfactants include but are not limited to the following surfactants: sodium trideceth sulfate, sodium tridecyl sulfate, sodium $C_{12-13}$ alkyl sulfate, sodium $C_{12-15}$ alkyl sulfate, sodium $C_{11-15}$ alkyl sulfate, sodium $C_{12-18}$ alkyl sulfate, sodium $C_{10-16}$ alkyl sulfate, sodium $C_{12-13}$ pareth sulfate, sodium $C_{12-13}$ pareth-n sulfate, and sodium $C_{12-14}$ pareth-n sulfate. Other salts of all the aforementioned surfactants are useful, such as TEA, DEA, ammonia, potassium salts. Useful alkoxylates include the ethylene oxide, propylene oxide and EO/PO mixed alkoxylates. Phosphates, carboxylates and sulfonates prepared from branched alcohols are also useful anionic branched surfactants. Branched surfactants can be derived from synthetic alcohols such as the primary alcohols from the liquid hydrocarbons produced by Fischer-Tropsch condensed syngas, for example Safol™ 23 Alcohol available from Sasol North America, Houston, Tex.; from synthetic alcohols such as Neodol™ 23 Alcohol available from Shell Chemicals, USA; from synthetically made alcohols such as those described in U.S. Pat. No. 6,335,312 issued to Coffindaffer, et al on Jan. 1, 2002. Preferred alcohols are Safol™ 23 and Neodol™ 23. Preferred alkoxylated alcohols are Safol™ 23-3 and Neodol™ 23-3. Sulfates can be prepared by conventional processes to high purity from a sulfur based $SO_3$ air stream process in a falling film reactor, chlorosulfonic acid process, sulfuric acid process, or Oleum process.

Monomethyl branched anionic surfactants include but are not limited to the branched anionic sulfates derived from Safol™ 23-n and Neodol™ 23-n as previously described, where n is an integer between 1 and about 20. Preferred monomethyl branched anionic surfactants include a $C_{12-13}$ alkyl sulfate derived from the sulfation of Safol™ 23, which has about 28% branched anionic surfactant molecules; and a C12-13 pareth sulfate derived from Neodol™ 23-3, which has about 10-18% branched anionic surfactant molecules.

Amphoteric surfactants are suitable for use in the multi-phase composition of the present invention. The amphoteric surfactants include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, and N-alkyltaurines.

Zwitterionic surfactants suitable for use include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Zwitterionic surfactants suitable for use in the multi-phase, personal cleansing composition include betaines, including cocoamidopropyl betaine.

Non-limiting examples of preferred nonionic surfactants for use herein are those selected form the group consisting of glucose amides, alkyl polyglucosides, sucrose cocoate, sucrose laurate, alkanolamides, ethoxylated alcohols and mixtures thereof. In a preferred embodiment the nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

Preferably the nonionic surfactant has an HLB from about 1.0 to about 15.0, preferably from about 3.4 to about 15.0, more preferably from about 3.4 to about 9.5, even more preferably from about 3.4 to about 5.0. The multi-phase personal cleansing composition preferably comprises a nonionic surfactant at concentrations ranging from about 0.01% to about 50%, more preferably from about 0.10% to about 10%, and even more preferably from about 0.5% to about 5.0%, by weight of the surfactant component.

Mixtures of anionic surfactants can be used in some embodiments, including mixtures of linear and branched surfactants, and anionic surfactants combined with nonionic, amphoteric, and/or zwitterionic surfactants.

An electrolyte, if used, can be added per se to the multi-phase personal cleansing composition or it can be formed in situ via the counterions included in one of the raw materials. The electrolyte preferably includes an anion comprising phosphate, chloride, sulfate or citrate and a cation comprising sodium, ammonium, potassium, magnesium or mixtures thereof. Some preferred electrolytes are sodium chloride, ammonium chloride, sodium or ammonium sulfate. The electrolyte is preferably added to the structured surfactant phase of the composition in the amount of from about 0.1% to about 15% by weight, preferably from about 1% to about 6% by weight, more preferably from about 3% to about 6%, by weight of the structured surfactant composition.

Benefit Phase: The multi-phase personal cleansing compositions of the present invention can comprise a benefit phase. The benefit phase in the present invention is preferably anhydrous and can be substantially free of water. The benefit phase can be substantially free of surfactant. The benefit phase of the present invention comprises a either a water in oil emulsion or an oil in water emulsion. In water in oil emulsions, the oil phase is the continuous phase and the water phase is the discontinuous or "internal" phase. In oil in water emulsions, the oil phase is the discontinuous phase and the water phase is the continuous or "internal" phase. As known in the art, a water in oil and oil in water emulsions comprises an aqueous phase; an oil; and an emulsifier.

The benefit phase of the present invention can comprise from about 10% to about 99%, more preferably from about 20% to about 95%, more preferably from about 50% to about 90%, and most preferably from about 60% to about 80% by weight of the benefit phase, of oil phase.

The hydrophobic materials and oils suitable for use in the benefit phase include any natural or synthetic materials with a Vaughan Solubility Parameter of from about 5 $(cal/cm^3)^{0.5}$ to about 15 $(cal/cm^3)^{0.5}$, some non-limiting examples of such oils include following: Cyclomethicone 5.92, Squalene 6.03, Petrolatum 7.33, Isopropyl Palmitate 7.78, Isopropyl Myristate 8.02, Castor Oil 8.90, Cholesterol 9.55, as reported in *Solubility, Effects in Product, Package, Penetration and Preservation*, C. D. Vaughan, Cosmetics and Toiletries, Vol. 103, October 1988. Preferably, the hydrophobic material has an overall solubility parameter of less than about 12.5 $(cal/cm^3)^{0.5}$ and preferably less than 11 $(cal/cm^3)^{0.5}$. By "overall solubility parameter" it is meant that one can use materials with higher solubility parameter blends with other materials with lower solubility parameters to reduce the overall solubility parameter. For example, a small portion of diethylene glycol with solubility parameter of 13.61 can be blended with lanolin oil with solubility parameter of 7.3 and a co-solubilizing agent to create a mixture with a solubility parameter of less than about 12.5 $(cal/cm^3)^{0.5}$.

Suitable for use herein are hydrophobic materials that include, but are not limited to the group consisting of petrolatum, lanolin, hydrocarbon oils (i.e. mineral oil), natural and synthetic waxes (i.e micro-crystalline waxes, paraffins, ozokerite, lanolin wax, lanolin alcohols, lanolin fatty acids, polyethylene, polybutene, polydecene and perhydrosqualen), volatile or non-volatile organosiloxanes and oganosiloxane derivatives (i.e. dimethicones, cyclomethicones, alkyl siloxanes, polymethylsiloxanes, and methylphenylpolysiloxanes), lanolin oil, esters (i.e. isopropyl lanolate, acetylated lanolin, acetylated lanolin alcohols, lanolin alcohol linoleate, lanolin alcohol riconoleate), natural and synthetic triglycerides (i.e. castor oil, soy bean oil, sunflower seed oil, maleated soy bean oil, safflower oil, cotton seed oil, corn oil, walnut oil, peanut oil, olive oil, cod liver oil, almond oil, avocado oil, palm oil and sesame oil) and combinations thereof.

Oil in Water Emulsifier: In embodiments of the benefit phase which are a oil in water emulsion the emulsifying agent typically comprise from about 0.1% to about 10% ,preferably from about 0.5% to about 5%, and more preferably from about 0.5% to about 3%, by weight of the benefit phase, of an emulsifier. Preferred oil in water emulsifers are those that reduce the surface tension of water to not less 60 mN/m at 25° C. as measured by standard surface tension apparati and methods known to those of ordinary skill in the art, for example ASTM D1331-89 (2001) Method A, "Surface Tension". Preferred emulsifiers exhibit a minimum surface tension in water of 60 mN/m or higher. Suitable emulsifiers promote stability of the oil in water emulsion by inhibiting coalescence of the oil droplets, and/or inhibiting phase separation of the oil and water phases.

Some suitable oil in water emulsifiers are Pemulen TR-1 (Acrylates/C10-30 Alkyl Acrylate Crosspolymer-Noveon), Pemulen TR-2 (Acrylates/C10-30 Alkyl Acrylate Crosspolymer-Noveon), ETD 2020 (Acrylates/C10-30 Alkyl Acrylate Crosspolymer-Noveon), Carbopol 1382 (Acrylates/C10-30 Alkyl Acrylate Crosspolymer-Noveon), Natrosol CS Plus 330, 430, Polysurf 67 (Cetyl Hydroxyethyl Cellulose-Hercules), Aculyn 22 (Acrylates/Steareth-20 Methacrylate Copolymer-Rohm&Haas) Aculyn 25 (Acrylates/Laureth-25 Methacrylate copolymer-Rohm&Haas), Aculyn 28 (Acrylates/Beheneth-25 Methacrylate copolymer-Rohm&Haas), Aculyn 46 (Peg-150/Stearyl Alcohol/SMDI copolymer-Rohm&Haas) Stabylen 30 (Acrylates/Vinyl Isodecanoate-3V), Structure 2001 (Acrylates/Steareth-20 Itaconate copolymer-National Starch), Structure 3001 (Acrylates/Ceteth-20 Itaconate copolymer-National Starch), Structure Plus (Acrylates/Aminoacrylates/C10-30 Alkyl Peg 20 Itaconate copolymer-National Starch, Quatrisoft LM-200 (Polyquaternium-24), the metal oxides of titanium, zinc, iron, zirconium, silicon, manganese, aluminium and cerium, polycarbonates, polyethers, polyethylenes, polypropylenes, polyvinyl chloride, polystyrene, polyamides, polyacrylates, cyclodextrins and mixtures thereof.

Other suitable emulsifiers include sub-micron organic or inorganic particles absorbed at the interface. Examples of suitable particles include micronized zeolite, fumed silica, titanium dioxide, zinc oxide, and aluminum oxide.

Water in Oil Emulsifiers: If the benefit phase is a water in oil emulsion, the benefit phase can comprise 0.1% to about 20%, more preferably from about 0.1% to about 10%, still more preferably from about 0.5% to about 9%, by weight of the benefit phase, of one or more emulsifiers.

Preferred water in oil emulsifiers of the present invention are selected from stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred emulsifiers of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred emulsifiers are selected from PEG-30 Dipolyhydroxystearate, Sorbitan Oleate and mixtures thereof. When using petrolatum alone or with mineral oil we have found mixtures of anionic/amphoteric and nonionic surfactants can be used to make water in oil emulsions. These surfactants include ammonium lauryl sulfate, ammonium laureth sulfate, sodium lauryl sulfate, sodium laureth sulfate, sodium tridecyl sulfate, sodium tridceth sulfate, sodium $C_{12-13}$ alkyl sulfate, sodium $C_{12-15}$ alkyl sulfate, sodium $C_{11-15}$ alkyl sulfate, sodium $C_{12-18}$ alkyl sulfate, sodium $C_{10-16}$ alkyl sulfate, sodium $C_{12-13}$ pareth sulfate, sodium $C_{12-13}$ pareth-n sulfate, and sodium $C_{12-14}$ pareth-n sulfate, sodium 3-dodecyl-aminopropionate, sodium 3-dodecylaminopropane sulfonate, sodium lauryl sarcosinate, N-alkyltaurines, cocoamidopropyl betaine, glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

Density Modifiers: The density modifier of the present invention can be comprised both the surfactant component and the benefit component or phase. These density modifiers are preferably low density microspheres. In composition with increased benefit component or phase where the volume fraction of lipid, a low density component, is increased to 50% in the same composition, the required Yield Stress of the composition calculated is 0.30 Pascal, due to the more stress per individual particle. Conventionally, one would expect that introducing other low density or more low density particles would destabilize the composition by increasing the stress on each individual particle.

However, introducing particular buoyant particles, density modifiers, to compositions comprising a dispersed hydrophobic benefit phase has a tendency to exert a stabilizing, not a destabilizing, effect on the composition. The stabilizing effect may be related to the density difference between the added buoyant particles and the dispersed hydrophobic benefit phase. For example, when the added buoyant particles have a density of about 25 kg/m$^3$ (i.e., 0.025 gm/cm$^3$), and the dispersed hydrophobic phase is petrolatum which has a density of about 0.88 gm/cm$^3$, the buoyant particles are 0.855 gm/cm$^3$ lower in density than the hydrophobic phase, leading to essentially 'superbuoyant regions' of composition comprising a buoyant particle and structured surfactant surrounding the particle, which reduces the gravitational force on the structured surfactant in the region adjacent to the particle. Preferably, the buoyant particles have a density of less than 0.85 gm/cm$^3$, more preferably less than about 0.5 gm/cm$^3$, still more preferably less than about 0.1 gm/cm$^3$, even more preferably less than about 0.05 gm/cm$^3$.

When the amount of a benefit component is increased in the composition; the need for density modifiers is also increased. Specifically, the need to add density modifier to the surfactant component is increased when (1) the benefit component is a hydrophobic material (petrolatum, e.g., having a lower density than the cleansing phase); (2) the amount of 'petrolatum' is higher than 20%, even 30%, even about 40% or more of the composition.

To further improve stability under stress conditions such as high temperature and vibration, it is preferable to adjust the densities of the separate components or phase, such that they are substantially equal. To achieve this, low density microspheres can be added to the cleansing phase of the benefit phase of the mild, structured, multi-phase cleansing composition. The low density microspheres employed to reduce the overall density of the surfactant component are particles having a density lower than 0.7 g/cm$^3$, preferably less than 0.2 g/cm$^3$, more preferably less than 0.1 g/cm$^3$, most preferably less than 0.05 g/cm$^3$. The low density microspheres generally have a diameter less than 200 μm, preferably less than 100 μm, most preferably less than 40 μm. Preferably, the density difference between the first density of the surfactant component when the surfactant component comprises the low density particles and the second density of the benefit component is less than 0.15 g/cm$^3$, more preferably, the density difference is less than 0.10 g/cm$^3$, even more preferably, the density difference is less than 0.08 g/cm$^3$, still more preferably, the density difference is less than 0.06 g/cm$^3$, still even more preferably, the density difference is less than 0.05 g/cm$^3$, most preferably, the density difference is less than 0.02 g/cm$^3$.

When the benefit component comprising hydrophobic materials such as petrolatum, mineral oil, waxes, hydrophobic polymers, fatty esters, fatty ethers, and/or triglycerides which have a density is blended with a structured surfactant component, the resulting blended composition has a density indicative of the mixture. For example, a multi-phase personal cleansing composition comprises 15% petrolatum having a density of 0.88 g/cm$^3$ mixed with a 85% of a surfactant component having a density of 1.0 g/cm$^3$ has a density of about 0.982 g/cm$^3$, but if the surfactant component utilizes low density particles to reduce its density to 0.93 g/cm$^3$, the resulting multi-phase personal cleansing composition has a density of about 0.923 g/cm$^3$. Preferably, the structured surfactant phase comprises low density particles so that the blended composition (i.e., hydrophobic benefit phase combined with surfactant phase) has a low density, preferably less than about 0.97 g/cm$^3$, more preferably less than about 0.96 g/cm$^3$, even more preferably less than about 0.95 g/cm$^3$, still more preferably less than about 0.94 g/cm$^3$, still even more preferably less than about 0.92 g/cm$^3$, most preferably less than about 0.90 g/cm$^3$.

Expanded microspheres made of thermoplastic material are known, and may be obtained, for example, according to the processes described in Patents and Patent Applications EP-56219, EP-348372, EP-486080, EP-320473, EP-112807 and U.S. Pat. No. 3,615,972. The microspheres are produced from any appropriate inorganic or organic material, compatible with a use on the skin, that is, nonirritating and nontoxic. These microspheres may be produced thermoplastic materials and can be in the dry or hydrated state. Among hollow microspheres which can be used, special mention may be made of those marketed under the brand name EXPANCEL® (thermoplastic expandable microspheres) by the Akzo Nobel Company, especially those of DE (dry state) or WE (hydrated state) grade. Representative microspheres derived from an inorganic material, include, for instance, "QCEL® Hollow Microspheres" and "EXTENDOSPHERES"™ Ceramic Hollow Spheres", both available from the PQ Corporation. Examples are: Qcel® 300; Qcel® 6019; Qcel® 6042S.

Just as low density microspheres can be added to the structured surfactant component of the present invention to improve stability, high density materials can be added to the benefit component to increase its density having the same impact on stability. The high density particles employed to increase the overall density of the benefit component are particles having a density greater than 1.1 g/cm$^3$, preferably greater than 1.5 g/cm$^3$, more preferably greater than 2.0 g/cm$^3$, most preferably greater than 2.5 g/cm$^3$. The high density particles generally have a diameter less than 200 μm, preferably less than 100 μm, most preferably less than 40 μm. Preferably, the high density particles are selected from water-insoluble inorganic materials, metals, metal oxides, metal alloys and mixture thereof. Non-limiting examples include calcium carbonate, silica, clays, mica, talc, iron, zinc, copper, lead, titanium dioxide, zinc oxide, and the like.

Additional Ingredients: Either phase of the multi-phase personal cleansing composition, can further comprise a polymeric phase structurant. The compositions of the present invention typically can comprise from about 0.05% to about 10%, preferably from about 0.1% to about 4%, by weight of the phase, of a polymeric phase structurant. Non-limiting examples of polymeric phase structurant include but are not limited to the following examples: naturally derived polymers, synthetic polymers, crosslinked polymers, block copolymers, copolymers, hydrophilic polymers, nonionic polymers, anionic polymers, hydrophobic polymers, hydrophobically modified polymers, associative polymers, and oligomers. Suitable polymeric phase structurants are more fully described in U.S. Pat. No. 5,087,445, to Haffey et al., issued Feb. 11, 1992; U.S. Pat. No. 4,509,949, to Huang et al., issued Apr. 5, 1985, U.S. Pat. No. 2,798,053, to Brown, issued Jul. 2, 1957. See also, CTFA International Cosmetic Ingredient Dictionary, fourth edition, 1991, pp. 12 and 80.

Either phase of the multi-phase personal cleansing compositions can further comprise a liquid crystalline phase inducing structurant, which when present is at concentrations ranging from about 0.3% to about 15%, by weight of the phase, more preferably at from about 0.5% to about 5% by weight of the phase. Suitable liquid crystalline phase inducing structurants include fatty acids (e.g. lauric acid, oleic acid, isostearic acid, linoleic acid) ester derivatives of fatty acids (e.g. propylene glycol isostearate, propylene glycol oleate, glyceryl isostearate) fatty alcohols, trihydroxystearin (available from Rheox, Inc. under the trade name THIXCIN® R). Preferably, the liquid crystalline phase inducing structurant is selected from lauric acid, trihydroxystearin, lauryl pyrrolidone, and tridecanol.

The multi-phase personal cleansing compositions can further comprise an organic cationic deposition polymer in the one or more phases as a deposition aid for the benefit agents described herein. Suitable cationic deposition polymers are more fully described in the co-pending and commonly assigned U.S. Patent Application No. 60/628,036 filed on Nov. 15, 2003 by Wagner, et al titled "Depositable Solids."

One or more phases of the multi-phase personal cleansing composition can comprise a variety of additional optional ingredients such as shiny particles, beads, exfoliating beads. Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992.

Other non limiting examples of these optional ingredients include vitamins and derivatives thereof (e.g., ascorbic acid, vitamin E, tocopheryl acetate), sunscreens; thickening agents, preservatives for maintaining the anti microbial integrity of the cleansing compositions, anti-acne medicaments, antioxidants, skin soothing and healing agents (i.e. aloe vera extract, allantoin), chelators, sequestrants and agents suitable for aesthetic purposes (i.e. fragrances, essential oils, skin sensates, lightning agents. pigments, pearlescent agents shiny particles, particles or beads, exfoliating beads, essential oils) and the like.

The preferred pH range of the structured multi-phase personal cleansing composition is from about 5 to about 8.

Method of Use: The mild, multi-phase cleansing compositions of the present invention are preferably applied topically to the desired area of the skin or hair in an amount sufficient to provide effective delivery of the structured surfactant component, hydrophobic benefit material, and particles to the applied surface. The compositions can be applied directly to the skin or indirectly via the use of a cleansing puff, washcloth, sponge or other implement. The compositions are preferably diluted with water prior to, during, or after topical application, and then subsequently the skin or hair rinsed or wiped off, preferably rinsed off of the applied surface using water or a water-insoluble substrate in combination with water.

Method of Manufacture: The multi-phase personal cleansing compositions of the present invention may be prepared by any known or otherwise effective technique, suitable for making and formulating the desired multi-phase product form. It is effective to combine toothpaste-tube filling technology with a spinning stage design. Additionally, the present invention can be prepared by the method and apparatus as disclosed in U.S. Pat. No. 6,213,166 issued to Thibiant, et al. on Apr. 10, 2001. The method and apparatus allows two or more compositions to be filled with a spiral configuration into a single container, requiring at least two nozzles be employed to fill the container. The container is placed on a static mixer and spun as the composition is introduced into the container.

Alternatively, it is effective to combine at least two phases by first placing the separate compositions in separate storage tanks having a pump and a hose attached. The phases are then pumped in predetermined amounts into a single combining section. From the combining section the phases are moved into the blending section and are blended such that the single resulting product exhibits a distinct pattern of the phases. Next, the resultant product is pumped by a single nozzle and filing the container with the resulting product.

Yield Stress and Zero Shear Viscosity Method: The Yield Stress and Zero Shear Viscosity of a phase of the present composition, can be measured either prior to combining in the composition, or after combining in the composition by separating the phase by suitable physical separation means, as described above.

A controlled stress rheometer such as a TA Instruments AR2000 Rheometer is used to determine the Yield Stress and Zero Shear Viscosity. The determination is performed at 25° C. with the 4 cm diameter parallel plate measuring system and a 1 mm gap. The geometry has a shear stress factor of 79580 $m^{-3}$ to convert torque obtained to stress.

First a sample of the phase is obtained and placed in position on the rheometer base plate, the measurement geometry (upper plate) moving into position 1 mm above the base plate. Excess phase at the geometry edge is removed by scraping after locking the geometry. If the phase comprises particles discernible to the eye or by feel (beads, e.g.) which are larger than about 150 microns in number average diameter, the gap setting between the base plate and upper plate is increased to the smaller of 4 mm or 8-fold the diameter of the $95^{th}$ volume percentile particle diameter. If a phase has any particle larger than 5 mm in any dimension, the particles are removed prior to the measurement.

The determination is performed via the programmed application of a continuous shear stress ramp from 0.1 Pa to 1,000 Pa over a time interval of 5 minutes using a logarithmic progression, i.e., measurement points evenly spaced on a logarithmic scale. Thirty (30) measurement points per decade of stress increase are obtained. Stress, strain and viscosity are recorded. If the measurement result is incomplete, for example if material flows from the gap, results obtained are evaluated and incomplete data points excluded. The Yield Stress is determined as follows. Stress (Pa) and strain (unitless) data are transformed by taking their logarithms (base 10). Log(stress) is graphed vs. log(strain) for only the data obtained between a stress of 0.2 Pa and 2.0 Pa, about 30 points. If the viscosity at a stress of 1 Pa is less than 500 Pa-sec but greater than 75 Pa-sec, then log (stress) is graphed vs. log (strain) for only the data between 0.2 Pa and 1.0 Pa, and the following mathematical procedure is followed. If the viscosity at a stress of 1 Pa is less than 75 Pa-sec, the zero shear viscosity is the median of the 4 highest viscosity values (i.e., individual points) obtained in the test, the yield stress is zero, and the following mathematical procedure is not used. The mathematical procedure is as follows. A straight line least squares regression is performed on the results using the logarithmically transformed data in the indicated stress region, an equation being obtained of the form: (1) Log(strain)=m*Log(stress)+b Using the regression obtained, for each stress value (i.e., individual point) in the determination between 0.1 and 1,000 Pa, a predicted value of log(strain) is obtained using the coefficients m and b obtained, and the actual stress, using Equation (1). From the predicted log(strain), a predicted strain at each stress is obtained by taking the antilog (i.e., $10^x$ for each x). The predicted strain is compared to the actual strain at each measurement point to obtain a % variation at each point, using Equation (2).

% variation=100*(measured strain−predicted strain)/measured strain  (2)

The Yield Stress is the first stress (Pa) at which % variation exceeds 10% and subsequent (higher) stresses result in even greater variation than 10% due to the onset of flow or deformation of the structure. The Zero Shear Viscosity is obtained by taking a first median value of viscosity in Pascal-seconds (Pa-sec) for viscosity data obtained between and including 0.1 Pa and the Yield Stress. After taking the first median viscosity, all viscosity values greater than 5-fold the first median value and less than 0.2× the median value are excluded, and a second median viscosity value is obtained of the same viscosity data, excluding the indicated data points. The second median viscosity so obtained is the Zero Shear Viscosity.

Ultracentrifugation Method: The Ultracentrifugation Method is used to determine the percent of a structured domain or an opaque structured domain that is present in a multi-phase personal cleansing composition that comprises a cleansing phase comprising a structured surfactant component. The method involves the separation of the composition by ultracentrifugation into separate but distinguishable layers. The personal cleansing composition of the present invention can have multiple distinguishable layers, for example a non-structured surfactant layer, a structured surfactant layer, and a benefit layer.

First, dispense about 4 grams of multi-phase personal cleansing composition into Beckman Centrifuge Tube (11× 60 mm). Next, place the centrifuge tubes in an Ultracentrifuge (Beckman Model L8-M or equivalent) and ultracentrifuge using the following conditions: 50,000 rpm, 18 hours, and 25° C.

After ultracentrifuging for 18 hours, determine the relative phase volume by measuring the height of each layer visually using an Electronic Digital Caliper (within 0.01 mm). First, the total height is measured as $H_a$ which includes all materials in the ultracentrifuge tube. Second, the height of the benefit layer is measured as $H_b$. Third, the structured surfactant layer is measured as $H_c$. The benefit layer is determined by its low moisture content (less than 10% water as measured by Karl Fischer Titration). It generally presents at the top of the centrifuge tube. The total surfactant layer height ($H_s$) can be calculated by this equation: $H_s=H_a-H_b$ The structured surfactant layer components may comprise several layers or a single layer. Upon ultracentrifugation, there is generally an isotropic layer at the bottom or next to the bottom of the ultracentrifuge tube. This clear isotropic layer typically represents the non-structured micellar surfactant layer. The layers above the isotropic phase generally comprise higher surfactant concentration with higher ordered structures (such as liquid crystals). These structured layers are sometimes opaque to naked eyes, or translucent, or clear. There is generally a distinct phase boundary between the structured layer and the non-structured isotropic layer. The physical nature of the structured surfactant layers can be determined through microscopy under polarized light. The structured surfactant layers typically exhibit distinctive texture under polarized light. Another method for characterizing the structured surfactant layer is to use X-ray diffraction technique. Structured surfactant layer display multiple lines that are often associated primarily with the long spacings of the liquid crystal structure. There may be several structured layers present, so that $H_c$ is the sum of the individual structured layers. If a coacervate phase or any type of polymer-surfactant phase is present, it is considered a structured phase.

Finally, the structured domain volume ratio is calculated as follows: Structured Domain Volume Ratio=$H_c/H_s$*100%. If there is no benefit phase present, use the total height as the surfactant layer height, $H_s=H_a$.

Lather Volume Test: Lather volume of a cleansing phase, a structured surfactant component or a structured domain of a structured multi-phase personal cleansing composition, is measured using a graduated cylinder and a rotating apparatus. A 1,000 ml graduated cylinder is used which is marked in 10 ml increments and has a height of 14.5 inches at the 1,000 ml mark from the inside of its base (for example, Pyrex No. 2982). Distilled water (100 grams at 25° C.) is added to the graduated cylinder. The cylinder is clamped in a rotating device, which clamps the cylinder with an axis of rotation that transects the center of the graduated cylinder. Inject 0.50 grams of a structured surfactant component or cleansing phase from a syringe (weigh to ensure proper dosing) into the graduated cylinder onto the side of the cylinder, above the water line, and cap the cylinder. When the sample is evaluated, use only 0.25 cc, keeping everything else the same. The cylinder is rotated for 20 complete revolutions at a rate of about 10 revolutions per 18 seconds, and stopped in a vertical position to complete the first rotation sequence. A timer is set to allow 15 seconds for lather generated to drain. After 15 seconds of such drainage, the first lather volume is measured to the nearest 10 ml mark by recording the lather height in ml up from the base (including any water that has drained to the bottom on top of which the lather is floating).

If the top surface of the lather is uneven, the lowest height at which it is possible to see halfway across the graduated cylinder is the first lather volume (ml). If the lather is so coarse that a single or only a few foam cells which comprise the lather ("bubbles") reach across the entire cylinder, the height at which at least 10 foam cells are required to fill the space is the first lather volume, also in ml up from the base. Foam cells larger than one inch in any dimension, no matter where they occur, are designated as unfilled air instead of lather. Foam that collects on the top of the graduated cylinder but does not drain is also incorporated in the measurement if the foam on the top is in its own continuous layer, by adding the ml of foam collected there using a ruler to measure thickness of the layer, to the ml of foam measured up from the base. The maximum lather height is 1,000 ml (even if the total lather height exceeds the 1,000 ml mark on the graduated cylinder). 30 seconds after the first rotation is completed, a second rotation sequence is commenced which is identical in speed and duration to the first rotation sequence. The second lather volume is recorded in the same manner as the first, after the same 15 seconds of drainage time. A third sequence is completed and the third lather volume is measured in the same manner, with the same pause between each for drainage and taking the measurement.

The lather results after each sequence are added together and the Total Lather Volume determined as the sum of the three measurements, in milliters ("ml"). The Flash Lather Volume is the result after the first rotation sequence only, in ml, i.e., the first lather volume. Compositions according to the present invention perform significantly better in this test than similar compositions in conventional emulsion form.

Density Method: The metal pycnometer is utilized for determination of density of the individual phases, the surfactant phase and the benefit phase compositions. Density is measured in the absence of confounding factors such as whipped air bubbles which are generally kept to a minimum in commercial processes. A metal pycnometer can be obtained from Fisher Scientific (USA). Following are the steps for measuring density of cleansing phase and benefit phase compositions, and the multi-phase personal cleansing composition. All instrument parts and phases are measured at ambient temperature.

The first step is cleaning: The metal pycnometer must be clean and dry before use. Disassemble the metal pycnometer completely and wash all parts well with water. Follow the water rinse with an alcohol rinse. Expel the alcohol with a stream of dry, clean air.

The second step is to obtain the weight of the empty pycnometer, and get pycnometer volume: Fill the clean, dry pycnometer with distilled water at 25 C. Place the lid on body of pycnometer and screw the cap firmly in place. Dry the outside of pycnometer well with a tissue and weigh to 0.001 g. Remove the water, clean and dry the pycnometer according to the directions shown above. Assemble and weigh the dry, empty pycnometer to 0.001 g to obtain the weight of empty pycnometer. Calculate the Water Weight in grams, which is numerically the pycnometer volume in $cm^3$, using the assumption that the density of water is 1.00 $g/cm^3$.

Water Weight=Weight of pycnometer filled with water−Weight of Empty Pycnometer.

The third step is the measurement of phase weight: Obtain a cleansing phase. The cleansing phase is preferably obtained prior to combining with a benefit phase, or it can be separated from a multi-phase composition by physical means such as centrifugation, pipetting, etc. The phase can contain a density modifier. Clean and dry the pycnometer according to the directions shown above. Pour or otherwise fill the phase into the pycnometer without introducing air, adding an excess of the phase so that it extends slightly above the top of the pycnometer. Screw the cap firmly onto the body of the pycnometer: excess is forced through the hole in the lid of the pycnometer. Wipe away the excess. Weigh the filled pycnometer to 0.001 g to obtain the Weight of Filled Pycnometer. Calculate the Phase Weight according to the following equation.

Phase Weight=Weight of Filled Pycnometer−Weight of Empty Pycnometer.

The fourth step is to calculate the Density of the phase according to the following equation:

Density of Phase=Sample Weight/Water Weight (express in $g/cm^3$).

The fifth step is repeat the procedure to obtain the Density of a benefit phase, using a benefit phase composition obtained by preparation of a phase, or by separation means.

The sixth step is to calculate the Density Difference: The Density Difference between the phases is calculated by subtracting the two values obtained for the Density of a Phase. Express the result as a positive number. When there are more than 2 phases present, three, or more than three, such Density Differences can be obtained by subtracting the values obtained in pairs.

Preferably, the Density Difference is less than 0.15 $g/cm^3$, more preferably, the Density Difference is less than 0.10 $g/cm^3$; even more preferably, less than 0.08 $g/cm^3$; still more preferably, is less than 0.06 $g/cm^3$; still even more preferably, less than 0.05 $g/cm^3$; and most preferably, the Density Difference is less than 0.02 $g/cm^3$.

EXAMPLES

The following examples further describe and demonstrate embodiments within the scope of the present invention, given solely for the purpose of illustration and are not to be construed as limitations of the present invention, as many variations thereof are possible without departing from the spirit and scope of the invention. Table 1 described examples of the cleansing phase of the multi-phase personal cleansing compositions of the present invention that are to be combined with the benefit phases described in Table 2.

TABLE 1

| Example of the Cleansing Phase (A) | |
| --- | --- |
| Materials | Weight Percent of Materials in Composition |
| Sodium Lauroamphoacetate (Cognis Chemical Corp.,) | 2.8 |
| Sodium Trideceth Sulfate (sulfated from Iconol TDA-3 (BASF Corp.) to >95% sulfate) | 4.8 |
| Sodium Lauryl Sulfate | 4.8 |
| Trideceth-3(Iconal TDA-3 from BASF Corp.) | 1.2 |
| Sodium Chloride | 2.5 |
| Guar hydroxypropyltrimonium chloride(N-Hance 3196 Polymer) | 0.33 |
| PEG 90M(Polyox WSR301) | 0.08 |
| Xanthan gum (Keltrol 1000, Kelco Corp.) | 0.14 |
| Expancel (091 WE 40 d24, from Expancel Inc.) | 0.25 |
| Methyl chloro isothiazolinone and methyl isothiazolinone (Kathon CG, Rohm & Haas) | 0.00032 |
| EDTA (Dissolvine NA 2x) | 0.09 |
| Sodium Benzoate | 0.12 |
| Citric Acid, titrate | pH = 5.7 ± 0.2 |
| Water | Q.S. |

TABLE 2

Examples of the Benefit Phase (B)

| Materials | Weight Percent of Materials in Composition Example Number | | | | | | | |
|---|---|---|---|---|---|---|---|---|
| | 1 | 2 | 3 | 4 | 5 | 6 | 7 | 8 |
| Petrolatum (from Quidesa, Mexico) | 21 | 18 | 30 | 25 | 8 | 8 | 25 | 20 |
| Mineral Oil (Hydrobrite 1000, WITCO) | 0 | 3 | — | 5 | — | — | — | 5 |
| Cleansing Phase (A) | 3.5 | 3.5 | — | — | — | — | — | — |
| PEG-30 Dipolyhydroxystearate (Arlacel P135 Uniqema) | — | — | 0.4 | 0.4 | 0.4 | 0.4 | 0.4 | 0.4 |
| Sorbitan Oleate (Span 80 Uniqema) | — | — | 1.6 | 1.6 | 1.6 | 1.6 | 1.6 | 1.6 |
| Water (internal phase) | 10.5 | 10.5 | 10.5 | — | 30 | 5 | 10.5 | — |
| Glycerine (internal phase) | — | — | — | 10.5 | — | 25 | — | 10.5 |
| Titanium Dioxide | — | — | — | — | — | — | 2 | — |
| Dihydroxyacetone | — | — | — | — | — | — | — | 5 |

Examples 1-2, which are the combination of the cleansing phase from Table 1 and the benefit phase from Table 2 can be prepared by conventional mixing techniques. Melt petrolatum at 80° C. and add mineral oil and pigment reduce temperature to 60° C. In a separate vessel, mix water, surfactant, salt and EDTA at room temperature. Add water phase slowly to oil phase with paddle mixing and bring temperature down to 45° C. continuing to mix. Add preservative and perfume and continue to mix. Cool the lipid premix to 100° F. and then add into the main batch. Adjust pH to 6.0. Keep agitation until homogeneous.

Examples 3-8 which are the combination of the cleansing phase from Table 1 and the benefit phase from Table 2 can be prepared by conventional mixing techniques. Melt petrolatum at 80° C. and add mineral oil, pigment, P135 and Span 80. In a separate vessel heat water to 75° C. and add salt and EDTA. Add water phase slowly to oil phase with paddle mixing and bring temperature down to 45° C. continuing to mix. Add preservative and perfume and continue to mix. The resulting W/O emulsion can be blended with the surfactant phase as described earlier.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein. All parts, ratios, and percentages herein, in the Specification, Examples, and Claims, are by weight and all numerical limits are used with the normal degree of accuracy afforded by the art, unless otherwise specified.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A mild, multi-phase personal cleansing composition comprising:
    (i) a cleansing phase comprising a structured surfactant component and water; said cleansing phase having a first density;
        wherein said structured surfactant component comprises low density microspheres having a density of less than 0.7 g/cm$^3$ and at least one surfactant; and wherein said structured surfactant component provides a Total Lather Volume of at least 600 ml;
    (ii) a benefit phase comprising an emulsion and optionally, high density particles having a density greater than 1.1 g/cm$^3$; said benefit phase having a second density;
    wherein said first density differs from said second density by less than 0.15 g/cm$^3$; and
    wherein the personal cleansing composition has a density of less than 0.97 g/cm$^3$.

2. The mild, multi-phase personal cleansing composition according to claim 1 wherein said low density microsphere is selected from the group consisting of inorganic material, organic material and mixtures thereof.

3. The mild, multi-phase cleansing composition of claim 1, wherein said structured surfactant component provides a Total Lather Volume of at least about 800 ml.

4. The mild, multi-phase cleansing composition of claim 1, wherein said structured surfactant component provides a Yield Point of greater than about 0.5 Pascal.

5. The mild, multi-phase cleansing composition of claim 1, comprising from about 1% to about 95%, by weight of the composition, of said structured surfactant component.

6. The mild, multi-phase cleansing composition of claim 1, wherein said surfactant is selected from the group consisting of anionic surfactant, nonionic surfactant, zwitterionic surfactant, cationic surfactant, amphoteric surfactant, soap, and mixtures thereof.

7. The mild, multi-phase cleansing composition of claim 6 wherein said anionic surfactant is selected from the group consisting of alkyl ether sulfates, alkyl sulfonates and mixtures thereof.

8. The mild, multi-phase cleansing composition of claim 6, wherein said amphoteric surfactant is selected from the group consisting of sodium lauroamphoacetate, sodium cocoamphoactetate, disodium lauroamphoacetate, and disodium cocodiamphoacetate, and mixtures thereof.

9. The mild, multi-phase cleansing composition of claim 6, wherein said nonionic surfactant is selected from the group consisting of glyceryl monohydroxystearate, steareth-2, propylene glycol stearate, sorbitan monostearate, glyceryl stearate, laureth-2, and mixtures thereof.

10. The mild, multi-phase cleansing composition of claim 6, comprising from about 0.1% to about 50%, by weight of said structured surfactant component, of said nonionic surfactant.

11. The mild, multi-phase cleansing composition of claim 10, wherein said nonionic surfactant has an HLB of from about 1.5 to about 15.0.

12. The mild, multi-phase cleansing composition of claim 1, wherein said composition comprises a structured domain wherein said structured domain is an opaque structured domain.

13. The mild, multi-phase cleansing composition of claim 12, wherein said opaque structured domain is a lamellar phase.

14. The mild, multi-phase cleansing composition of claim 1, wherein said composition is substantially free of an alkyl amines and an alkanolamides.

15. The mild, multi-phase cleansing composition of claim 1, wherein said emulsion is a water in oil emulsion.

16. The mild, multi-phase cleansing composition of claim 1, wherein said emulsion is an oil in water emulsion.

17. The mild, multi-phase cleansing composition of claim 1, wherein the benefit phase comprises 20%-40% of a hydrophobic material.

18. The mild, multi-phase cleansing composition of claim 1, wherein the benefit phase comprises at least 40% of a hydrophobic material.

19. A mild, multi-phase personal cleansing composition comprising:
(i) a cleansing phase comprising a structured surfactant component and water; said cleansing phase having a first density;
wherein said structured surfactant component comprises low density microspheres having a density of less than 0.7 g/cm$^3$ and at least one surfactant;
(ii) a benefit phase comprising an emulsion; said benefit phase having a second density;
wherein the benefit phase comprises at least 20% of a hydrophobic material and
optionally, high density particles having a density greater than 1.1 g/cm$^3$;
wherein said first density differs from said second density by less than 0.06 g/cm$^3$; and
wherein the personal cleansing composition has a density of less than 0.90 g/cm$^3$.

20. A mild, multi-phase personal cleansing composition of claim 17, wherein said structured surfactant component provides a Total Lather Volume of at least 800 ml.

* * * * *